United States Patent [19]
Wengyn et al.

[11] Patent Number: 5,184,721
[45] Date of Patent: Feb. 9, 1993

[54] HYPODERMIC NEEDLE/SYRINGE RECEPTACLE WITH POROUS ELEMENT

[76] Inventors: Mark D. Wengyn, 1543 Highcrest Cir.; Charles F. Brown, 2201 Cherokee Trail, both of Valrico, Hillsborough County, Fla. 33594

[21] Appl. No.: 819,057

[22] Filed: Jan. 10, 1992

[51] Int. Cl.⁵ .............................................. A61L 2/16
[52] U.S. Cl. .................................... 206/366; 206/443; 206/571; 211/60.1; 422/301
[58] Field of Search .................. 422/300, 301, 310; 206/204, 363-366, 571, 443, 446; 248/219.3, 311.2; 211/60.1

[56] References Cited

U.S. PATENT DOCUMENTS

| | | | |
|---|---|---|---|
| 478,081 | 7/1892 | Botsford | 206/365 X |
| 920,225 | 5/1909 | Van Denburgh et al. | 206/364 X |
| 2,012,380 | 8/1935 | Durham | 206/365 X |
| 2,093,537 | 9/1937 | Balirt | 206/365 X |
| 2,925,100 | 2/1960 | Senger | 206/363 X |
| 2,935,285 | 5/1960 | Drom | 248/219.3 |
| 3,292,776 | 12/1966 | Penn | 206/366 X |
| 4,015,810 | 4/1977 | Williams | 248/311.2 |
| 4,037,814 | 7/1977 | Clausen | 248/311.2 |
| 4,936,449 | 6/1990 | Conard et al. | 206/366 |
| 5,020,665 | 6/1991 | Bruno | 206/366 |
| 5,024,865 | 6/1991 | Insley | 206/443 X |
| 5,029,699 | 7/1991 | Insley et al. | 206/204 |

OTHER PUBLICATIONS

"Roll Covering Handbook" excerpt, IP-5 1980.

Primary Examiner—Bryon P. Gehman
Attorney, Agent, or Firm—Arthur W. Fisher, III

[57] ABSTRACT

A hypodermic needle/syringe receptacle to support and retain a plurality of hypodermic needle/syringe combinations to prevent the accidental pricking of the care giver or patient after use comprising an outer receptacle support including a substantially cylindrical body having a centrally disposed substantially cylindrical canister recess and a plurality of peripherally disposed substantially cylindrical liquid retaining tube recesses formed therein to selectively receive and support an inner disinfectant canister and a plurality of substantially cylindrical liquid retaining tubes respectively wherein the inner disinfectant retaining canister includes a substantially cylindrical tube to operatively house a disinfectant therein and a penetrable membrane to receive the used hypodermic needle/syringe combinations therethrough to support and retain the used hypodermic needles in the disinfectant for subsequent disposal.

17 Claims, 3 Drawing Sheets

HYPODERMIC NEEDLE/SYRINGE RECEPTACLE WITH POROUS ELEMENT

BACKGROUND OF THE INVENTION

1. Field of the Invention

A receptacle to support and retain a plurality of hypodermic needle/syringe combinations to prevent the accidental pricking of the care giver or patient after use for safe storage and disposal.

2. Description of the Prior Art

Numerous means for the disposal of contaminated medical instruments have been developed. Such devices often provide containers to receive contaminated medical instruments deposited for disposal. It is important that such disposal devices reduce the extent reasonably obtainable the likelihood that the contaminated medical instruments will subsequently accidentally puncture someone and that contaminants will escape from the disposal container.

U.S. Pat. No. 4,919,264 describes a medical needle removing and disposing system comprising a box having a plurality of compartments therein, each for removing a needle assembly from injection and/or blood drawing equipment and for disposing of the needle assembly. A compartment comprises first and second containers for defining first and second chambers with a needle gripper positioned therebetween. The first container has a plastic, non-hardening, tacky, substance therein. Injection and/or blood drawing equipment with a medical needle assembly mounted thereon can be manipulated to extend a shaft of the needle assembly into the second chamber until a mounting tube of the medical needle assembly is located at the needle assembly remover which grips the mounting tube so that the injection and/or blood drawing equipment can be rotated for unscrewing the mounting tube from the injection and/or blood drawing equipment. The medical needle assembly is left in the dispenser with the shaft buried in the tacky substance.

U.S. Pat. No. 4,936,449 shows a block of syrofoam for penetration by and for frictionally holding, disposable hypodermic needles and scalpes held in a container including a bottom and a side wall. Pawl-shaped projections are provided adjacent the upper lip of the sidewall. A lid includes complementary pawl-shaped projections adjacent its lower lip for engagement with respective projections on a contaminant neutralizing substance such as BETADINE, or another layer of, for example, wadding, located above or below the styrofoam can be saturated with the contaminant neutralizing substance.

U.S. Pat. No. 3,876,067 describes a collection box having a cover plate provided with a multiplicity of square openings into which a needle is inserted detachably fastened at a one-way-syringe whereby the head of the needle is caught behind the sharp-edged inside border of the opening and the syringe can be pulled off from the needle which is being held in position by a disinfectant filling into which the needle has been pierced.

U.S. Pat. No. 2,935,285 teaches an injection syringe container comprising a housing having a bottom wall, side walls, first and second end walls and a top wall. The top wall is formed with a longitudinal row of spaced opdNings, a pair of facing channel tracks secured upon and extending along the top wall and located at opposite sides of the longitudinal row of openings with upstanding tubes within the housing and fixedly mounted on the bottom wall.

Additional examples of the prior art are found in U.S. Pat. Nos. 2,738,872; 4,327,060; 4,380,292; Des. 229,048 and Des. 259,141.

SUMMARY OF THE INVENTION

The present invention relates to a hypodermic needle/syringe receptacle to support and retain a plurality of hypodermic needle/syringe combinations to prevent the accidental pricking of the care giver or patient after use comprising an outer receptacle support configured to support an inner disinfectant canister and plurality of liquid retaining tubes in combination with a mounting means to mount the hypodermic needle/syringe receptacle on a wall or other supporting surface.

The outer receptacle support comprises a substantially cylindrical body including a centrally disposed substantially cylindrical canister recess to selectively receive and support the inner disinfectant canister and a plurality of peripherally disposed substantially cylindrical liquid retaining tube recesses to selectively receive and support the plurality of liquid retaining tubes.

The inner disinfectant canister comprises a substantially cylindrical tube to operatively house a disinfectant therein and penetrable membrane to receive the used hypodermic needles therethrough to support and retain the used hypodermic needle/syringe combinations in the disinfectant.

The mounting means comprises a substantially cylindrical mounting sleeve to selectively secure the outer receptacle support and inner disinfectant canister to a wall or other support surface.

With the mounting means affixed to a wall or other supporting surface, the outer receptacle support and inner disinfectant canister are operatively mounted thereon.

In use, the care taker withdraws blood or other body fluids that are injected into one or more of the plurality of liquid retaining tubes operatively supported in the outer receptacle support. As the care taker has completed using the hypodermic needle/syringe combination, the hypodermic needle is forced through the penetrable membrane into the substantially cylindrical tube and submerged in the disinfectant to prevent accident or inadvertant contact with the care taker or patient. Ultimate the plurality of liquid retaining tubes may be removed from the outer receptacle support for testing of the liquids stored therein and the inner disinfectant canister may be removed from the outer receptacle support for disposal of the used hypodermic needle/syringe combinations.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
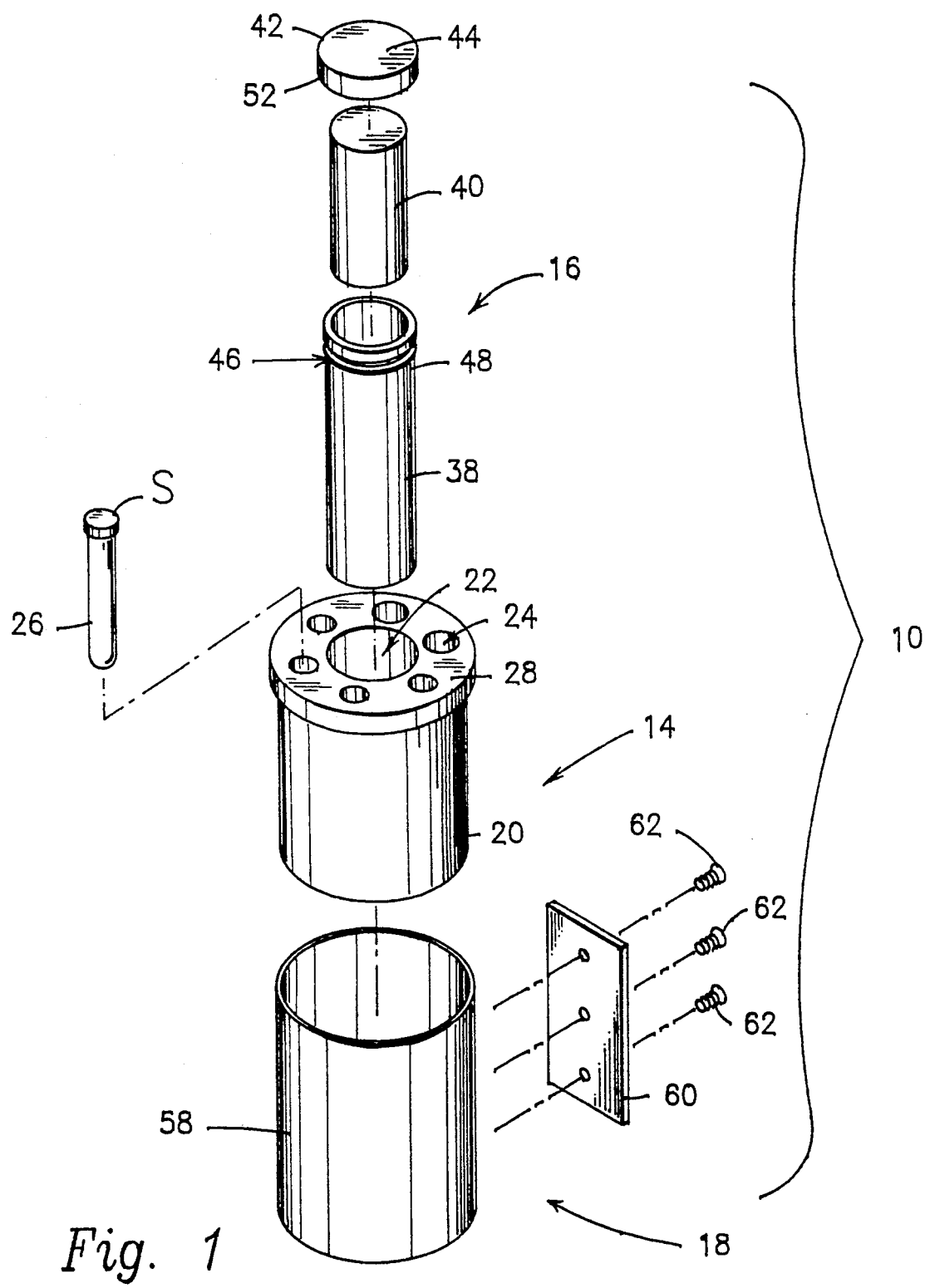
FIG. 1 is an exploded view of the hypodermic needle/syringe receptacle of the present invention.
Figure 2:
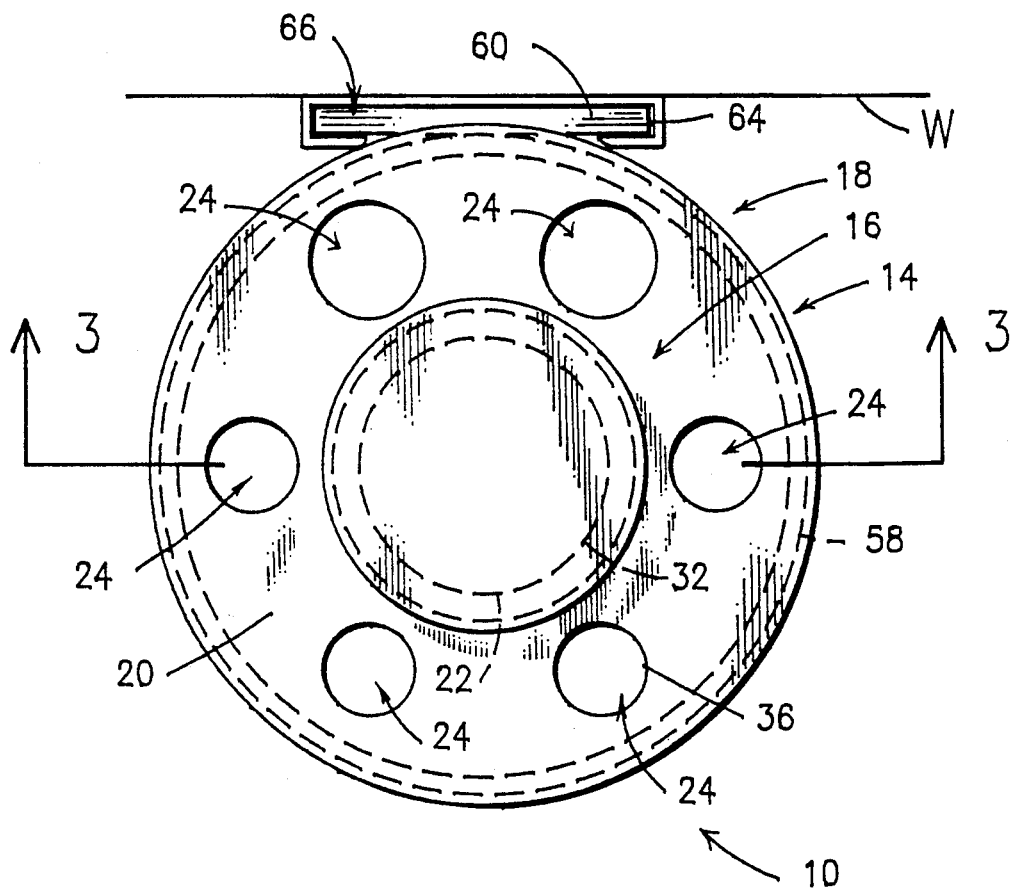
FIG. 2 is a top view of the hypodermic needle/syringe receptacle of the present invention.

As best shown in FIGS. 1 and 2, the present invention relates to a hypodermic needle/syringe receptacle generally indicated as 10 to support a plurality of hypodermic needle/syringe combinations each generally indicated as 12 to prevent the accidental or inadvertant pricking of the care taker or patient after use.

Figure 3:
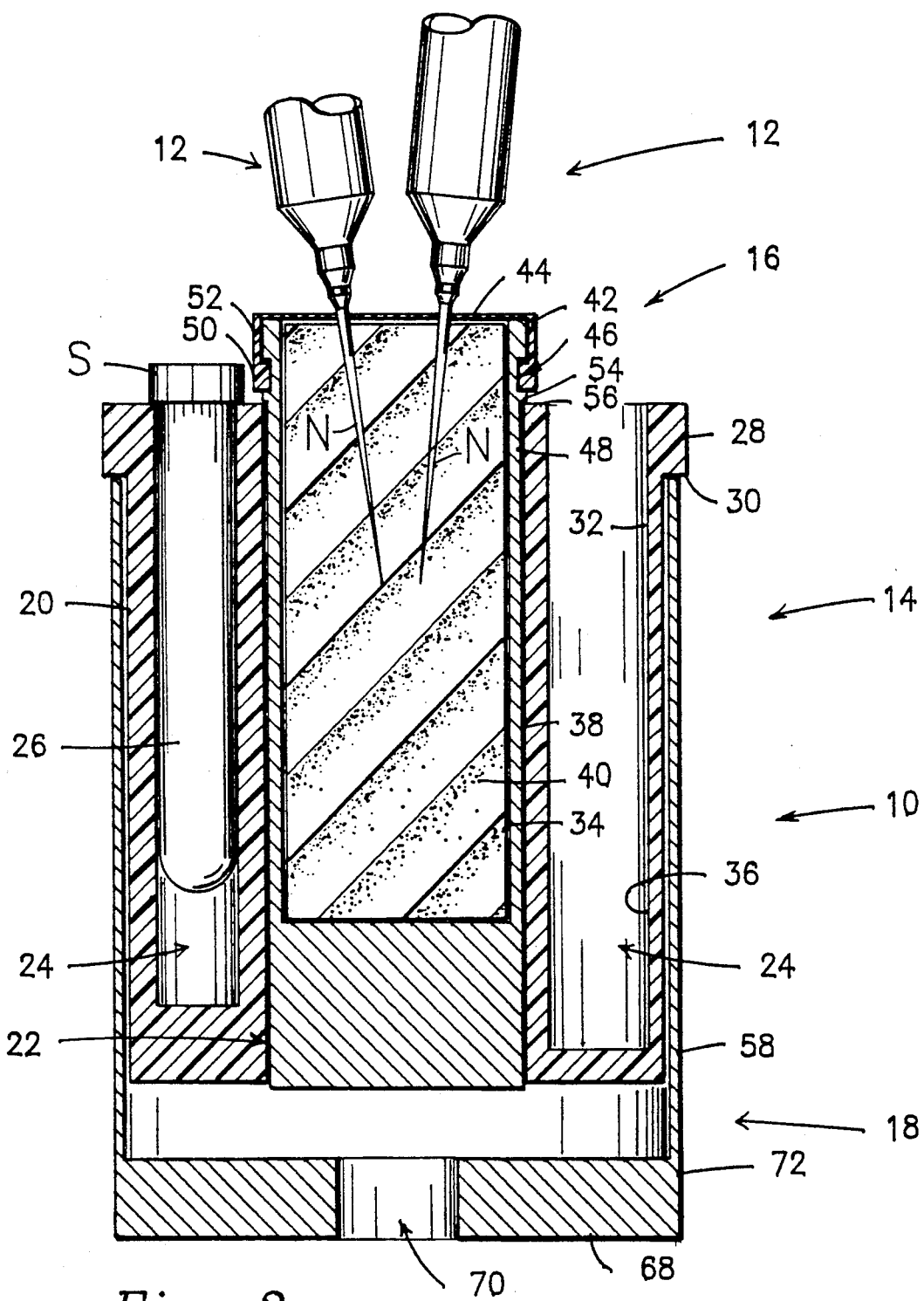
FIG. 3 is a cross-section of the hypodermic needle/syringe receptacle of the present invention taken along line 3—3 of FIG. 2.

As shown in FIGS. 1 through 3, the hypodermic needle/syringe receptacle 10 comprises an outer receptacle support generally indicated as 14, an inner disinfectant canister generally indicated as 16 and a mounting means generally indicated as 18.

As best shown in FIGS. 1 and 2, the outer receptacle support 14 comprises a lower substantially cylindrical body 20 including a centrally disposed substantially cylindrical canister recess 22 extending the entire length thereof and a plurality of peripherally disposed substantially cylindrical liquid retaining tube recesses each indicated as 24 configured to selectively receive and support the inner disinfectant canister 16 and a plurality of liquid retaining tubes each indicated as 26 respectively. An upper receptacle support 28 comprising a support surface or ledge 30 is formed about the upper periphery 32 of the lower substantially cylindrical body 20 to engage the mounting means 18 when the outer receptacle support 14 is mounted thereon. The outer receptacle support 14 is constructed of 60 durometer urethane This provides sufficient strength and resilience to protect the inner disinfectant canister 16 and liquid retaining tubes 26, while having adequate memory such that the interior wall of the centrally disposed substantially cylindrical canister recess 22 and the interior walls of the plurality of peripherally disposed substantially cylindrical liquid tube recesses 24 indicated as 34 and 36 respectively are resilient to engage and secure the inner disinfectant canister 16 and liquid retaining tubes 26 with the centrally disposed substantially cylindrical canister means 22 and the plurality of peripherally disposed substantially cylindrical liquid tube recesses 24 respectively.

As best shown in FIGS. 1 and 3, the inner disinfectant canister 16 comprising a substantially cylindrical tube 38 to operatively house a pourous element 40 of wet foam permeated with a disinfectant and a closure cap 42 including a penetrable membrane 44 to receive the used hypodermic needles each indicated as N therethrough to support and retain the used hypodermic needles N in the disinfectant. An annular groove 46 is formed about the upper periphery 48 of the substantially cylindrical tube 38 to operatively receive an annular lip 50 extending inwardly from an annular skirt 52 extending downwardly from the penetrable membrane 44 to secure the closure cap 42 to the substantially cylindrical tube 38. A support ledge 54 extends outwardly from the upper periphery 48 of the substantially cylindrical tube 38 to engage the upper edge 56 of the centrally disposed substantially cylindrical recess 22. The penetrable membrane 44 is substantially one-sixteenth (1/16") inches in thickness of urethane of between 25 and 30 durometers. This particular thickness and hardness permits relative easy penetration of the penetrable membrane 44 by the needles N without tearing and strong enough to support the hypodermic needle/syringe combinations 12 in a substantially vertical orientation or disposition.

As shown in FIGS. 1 through 3, the mounting means 18 comprises a substantially cylindrical mounting sleeve 58 to receive the lower substantially cylindrical body 20 therein, a mounting plate 60 fixed to the rear portion of the substantially cylindrical mount sleeve 58 by rivets 62 or the like and a mounting bracket 64 including a slot 66 to selectively receive the mounting plate 60 therein. A floor or bottom 68 having a centrally disposed aperture 70 formed therethrough may be formed across the lower periphery 72 of the substantially cylindrical mounting sleeve 58.

With the mounting means 18 attached to a wall W or other supporting surface, the outer receptacle support 14 and inner disinfectant canister 16 are operatively mounted thereon.

In use, the care taker withdraws blood or other body fluids that are injected through stoppers S into one or more of the plurality of liquid retaining tubes 26 operatively supported in the outer receptacle support 14. As the care taker has completed using the hypodermic needle/syringe combination 12, the hypodermic needle N is forced through the penetrable membrane 44 into the substantially cylindrical tube 38 and submerged in the disinfectant and retained in the porous element 40 to prevent accidental or inadvertant contact with the care taker or patient. Excess body or other body fluids may be injected into the substantially cylindrical tube 38. Moreover, the porous element 40 plugs the distal ends of the needles N. The substantially cylindrical mounting sleeve 58, outer receptacle support 14 and inner disinfectant canister 16 are removed from the mounting bracket 64. The plurality of liquid retaining tubes 26 may be removed from the outer receptacle support 14 for testing of the liquids stored therein and the inner disinfectant canister 16 may be removed from the outer receptacle support 14 for disposal of the used hypodermic needle/syringe combinations 12.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A receptacle to support and retain a plurality of used hypodermic needle and syringe combinations and a plurality of hollow tubes, said receptacle comprising an outer receptacle support including a centrally-disposed canister recess housing a hollow inner canister having a porous element disposed therein and a plurality of peripherally-disposed tube recesses housing a corresponding plurality of hollow tubes such that body fluids drawn from a patient by a hypodermic needle and syringe combination are injected into one or more of the hollow tubes for storage and transport, and wherein used hypodermic needle and syringe combinations are mounted on said receptacle by imbedding the needles of the used hypodermic needle and syringe combinations into said porous element to securely retain the used hypodermic and needle combination on said receptacle.

2. The receptacle of claim 1 wherein said porous element comprises a member permeated with a disinfectant solution to receive the used hypodermic needles therethrough to support and retain the used hypodermic needles in the disinfectant solution.

3. The receptacle of claim 2 wherein said hollow inner canister comprises an open tube having a cap including a penetrable membrane mounted on said open tube to retain the disinfectant solution and excess body fluids therein wherein said penetrable membrane receives used hypodermic needles therethrough.

4. The receptacle of claim 3 wherein aid hollow inner canister includes an annular groove formed about the upper portion thereof to operatively receive an annular lip extending inwardly from an annular skirt extending downwardly from said penetrable membrane to secure said cap to said open tube.

5. The receptacle of claim 4 wherein said hollow inner canister includes a support ledge extending outwardly from the upper periphery thereof in spaced relationship relative to said annular groove to engage the upper edge of said outer receptacle support.

6. The receptacle of claim 3 wherein said penetrable membrane is constructed of urethane between 25 and 30 durometers to seal said penetrable membrane when the used hypodermic needles pass through said penetrable membrane into said porous element.

7. The receptacle of claim 6 wherein said penetrable membrane is one-sixteenth of an inch in thickness.

8. The receptacle of claim 1 further including a mounting means comprising a mounting sleeve to support said outer receptacle support therein and a mounting plate attached to said mounting sleeve to secure said receptacle to a support surface.

9. The receptacle of claim 8 wherein aid outer receptacle support includes an upper receptacle support formed about the upper periphery thereof to engage the upper periphery of said mounting sleeve to support said outer receptacle support thereon.

10. A receptacle to support and retain a plurality of used hypodermic needle and syringe combinations, said receptacle comprising an outer receptacle comprising an outer receptacle support including a centrally-disposed canister recess housing a hollow inner canister, the canister having a cap mounted thereon and the cap including a penetrable membrane to receive used hypodermic needles therethrough and a porous element disposed in the canister such that used hypodermic needle and syringe combinations are mounted on said receptacle by imbedding the needles of the used hypodermic needle and syringe combinations into said porous element to securely retain the used hypodermic and needle combinations on said receptacle.

11. The receptacle of claim 10 wherein said porous element comprises a member permeated with a disinfectant solution to receive the used hypodermic needles therethrough to support and retain the sued hypodermic needles in the disinfectant.

12. The receptacle of claim 10 wherein said cap includes an annular skirt extending downwardly from said penetrable membrane and said hollow inner canister includes an annular groove formed about the upper portion thereof to operatively receive an annular lip extending inwardly from said annular skirt to secure said cap to said open tube.

13. The receptacle of claim 12 wherein said hollow inner canister includes a support ledge extending outwardly from the upper periphery thereof in spaced relationship relative to said annular groove to engage the upper edge of said outer receptacle support.

14. The receptacle of claim 10 wherein said penetrable membrane is constructed of urethane having a hardness between 25 and 30 durometers to seal said penetrable membrane when used hypodermic needles pass through said penetrable membrane into said porous element.

15. The receptacle of claim 14 wherein said penetrable membrane is one-sixteenth of an inch in thickness.

16. The receptacle of claim 10 further including a mounting means comprising a mounting sleeve to support said outer receptacle support therein and a mounting plate attached to said mounting sleeve to secure said receptacle to a support surface.

17. The receptacle of claim 16 wherein said outer receptacle support includes an upper receptacle support formed about the upper periphery thereof to engage the upper periphery of said mounting sleeve to support said outer receptacle support.

* * * * *